(12) United States Patent
Edwards et al.

(10) Patent No.: US 8,858,917 B2
(45) Date of Patent: Oct. 14, 2014

(54) METHODS FOR LIMITING SPREAD OF PULMONARY INFECTIONS

(75) Inventors: David A. Edwards, Boston, MA (US); Howard A. Stone, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 872 days.

(21) Appl. No.: 12/351,328

(22) Filed: Jan. 9, 2009

(65) Prior Publication Data

US 2009/0208581 A1    Aug. 20, 2009

Related U.S. Application Data

(63) Continuation of application No. 10/513,165, filed as application No. PCT/US03/13707 on May 1, 2003.

(60) Provisional application No. 60/377,327, filed on May 2, 2002.

(51) Int. Cl.
*A61K 9/00* (2006.01)
*A61K 31/685* (2006.01)
*A61K 9/14* (2006.01)
*A61K 31/74* (2006.01)
*A61K 31/355* (2006.01)
*A61K 31/715* (2006.01)

(52) U.S. Cl.
CPC ............. *A61K 9/0075* (2013.01); *A61K 31/685* (2013.01); *A61K 31/715* (2013.01); *A61K 31/355* (2013.01); *A61K 9/0078* (2013.01)
USPC ...... 424/46; 424/1.13; 424/78.08; 424/78.37; 424/489; 424/499; 424/501; 424/502; 514/12; 514/54; 514/59; 530/350; 530/362; 536/112; 536/123.1; 128/200.14

(58) Field of Classification Search
USPC .......... 424/1.13, 78.08, 78.37, 434, 489, 499, 424/501, 502, 43, 45, 46; 514/12, 54, 59; 530/350, 362; 536/123.1, 112; 128/200.14
See application file for complete search history.

(56) References Cited

U.S. PATENT DOCUMENTS

| 4,828,844 | A | 5/1989 | Rontgen-Odenthal et al. |
| 5,175,152 | A | 12/1992 | Singh |

(Continued)

FOREIGN PATENT DOCUMENTS

| EP | 0 367 723 | 5/1990 |
| EP | 0652011 | 5/1995 |

(Continued)

OTHER PUBLICATIONS

Feng, et al., "Improved clearability of cystic fibrosis sputum with dextran treatment in vitro", Am. J. Respir. Crit. Care Med., 157(3):710-714 (1998).

(Continued)

*Primary Examiner* — Jane C Oswecki
(74) *Attorney, Agent, or Firm* — Pabst Patent Group LLP

(57) ABSTRACT

Formulations have been developed for pulmonary delivery to treat or reduce the infectivity of diseases such as vital infections, especially tuberculosis, SARS, influenza and respiratory synticial virus in humans and hoof and mouth disease in animals. Formulations for pulmonary administration include a material that significantly alters physical properties such as surface tension and surface elasticity of lung mucus lining fluid, which may be a surfactant and, optionally, a carrier. The formulation may be administered as a powder where the particles consist basically of the material altering surface tension. The carrier may be a solution, such as an alcohol, although an aqueous solution may be utilized, or a material mixed with the material altering surface tension to form particles. These may include proteins such as albumin or polysaccharides such as dextran, which also has surface active properties, or polymers such as polyethylene oxide (PEO) or biodegradable synthetic polymers which can be used to encapsulate or deliver the materials to be delivered. Drugs, especially antivirals or antibiotics, may optionally be included with the formulation. These may be administered with or incorporated into the formulation.

10 Claims, 9 Drawing Sheets

(56) References Cited

U.S. PATENT DOCUMENTS

| | | | |
|---|---|---|---|
| 5,230,884 A | | 7/1993 | Evans et al. |
| 5,466,680 A | | 11/1995 | Rudy |
| 5,514,665 A | * | 5/1996 | Speert et al. ............... 514/53 |
| 5,633,003 A | | 5/1997 | Cantor |
| 5,654,007 A | | 8/1997 | Johnson et al. |
| 5,709,202 A | | 1/1998 | Lloyd et al. |
| 5,817,028 A | | 10/1998 | Anderson |
| 5,855,912 A | * | 1/1999 | Ortyl et al. ............... 424/452 |
| 5,855,913 A | * | 1/1999 | Hanes et al. ............... 424/489 |
| 5,883,084 A | | 3/1999 | Peterson et al. |
| 5,985,309 A | | 11/1999 | Edwards et al. |
| 6,083,922 A | | 7/2000 | Montgomery |
| RE37,053 E | | 2/2001 | Hanes et al. |
| 6,214,536 B1 | | 4/2001 | Boucher, Jr. |
| 6,339,075 B1 | * | 1/2002 | King et al. ............... 514/59 |
| 6,669,959 B1 | * | 12/2003 | Adjei et al. ............... 424/489 |
| 8,187,637 B2 | * | 5/2012 | Edwards et al. ............... 424/489 |
| 2001/0008632 A1 | | 7/2001 | Freund et al. |
| 2002/0177562 A1 | | 11/2002 | Weickert et al. |
| 2004/0009128 A1 | | 1/2004 | Rabinowitz et al. |
| 2007/0270502 A1 | | 11/2007 | Edwards et al. |
| 2007/0275091 A1 | | 11/2007 | King et al. |
| 2008/0038207 A1 | | 2/2008 | Edwards et al. |

FOREIGN PATENT DOCUMENTS

| | | |
|---|---|---|
| WO | WO 92/06695 | 4/1992 |
| WO | WO 96/12470 | 5/1996 |
| WO | 9729738 | 8/1997 |
| WO | WO 97/36574 | 10/1997 |
| WO | WO 97/44013 | 11/1997 |
| WO | 9831346 | 7/1998 |
| WO | 0205730 | 1/2002 |
| WO | WO 02/05730 | 1/2002 |
| WO | WO 02/09574 | 2/2002 |
| WO | WO 03/092654 | 11/2003 |

OTHER PUBLICATIONS

Zayas, et al., "A new paradigm in respiratory hygene: modulating respiratory secretions to contain cough bioaerosol without affecting mucus clearance", BMC Pulm. Med., 7:11 (2007).
Adjei and Garren, "Pulmonary delivery of peptide drugs: Effect of particle size on bioavailability of leuprolide acetate in healthy male volunteers", Pharm. Res., 7:565-569 (1990).
Aldrich Chemical Catalog, 1998-1999, pp. 1502.
Anderson, et al., "Effect of cystic fibrosis on inhaled aerosol boluses", Am. Rev. Respir. Dis., 140: 1317-1324 (1989).
Bergeron, et al., "Controlling droplet deposition with polymer additives", Nature, 405:772-775 (2000).
Boren, "The development of a molecular model of lung", Arch. Intern. Med., 126(3):491-495) (1970).
Bromberg and Klibanov, "Transport of proteins dissolved in organic solvents across biomimetic membranes", Proc. Natl. Acad. Sci. USA, 92(5):1262-6 (1995).
Cataldo, et al., "Induced sputum: comparison between isotonic and hypertonic saline solution inhalation in patients with asthma", Chest, 120(6):1815-21 (2001).
Choi, et al., "Inhalation delivery of proteins from ethanol suspensions", Proc. Natl. Acad. Sci. USA, 98:11103-11107 (2001).
Clarke, et al., "Resistance to two-phase gas-liquid flow in airways", J. Appl. Physiol., 29(4): 464-471(1970).
Edwards, "The macrotransport of aerosol particles in the lung: aerosol deposition phenomena", J. Aerosol Sci., 26:293-317 (1995).
Evrensel, et al., "Viscous airflow through a rigid tube with a compliant lining: A simple model for the air-mucus interaction in pulmonary pathways", J. Biomech. Eng., 115:262-27 (1993).
Ferguson, et al., "Transmission intensity and impact of control policies on the foot and mount epidemic in Great Britain", Nature, 414(6861): 329 (2001).
French, et al., "The influence of formulation on emission, deaggregation and deposition of dry powders for inhalation", J. Aerosol Sci., 27: 769-783 (1996).

Fuge, et al, "The geochemistry of iodine —a review", Environmental Geochemistry and Health, 8(2): 31-54 (1986).
Gad-El-Hak, et al., "On the interaction of compliant coatins with boundary-layer flows", J. Fluid Mech., 140: 257-280 (1984).
Ganderton, "The generation of respirable clouds form coarse powder aggregates", Journal of Biopharmaceutical Sciences, 3(1/2):101-105 (1992).
Gonda, "Aerosols for delivery of therapeutic and diagnostic agents to the respiratory tract", Critical Reviews in Therapeutic Drug Carrier Systems, 6:273-313 (1990).
Hardy, et al., "Sensitivity of aerosol bolus behavior to methacholine-induced bronchoconstriction", Chest, 114(2):404-10 (1998).
Hawley's Condensed Chemical Dictionary, $14^{th}$ Edition, John Wiley & Sons, Inc., 2001 pp. 161 and 977.
Heyder, et al., "Deposition of particles in the human respiratory tract in the size range 0.005-15µm", J. Aerosol Sci., 17: 811-825 (1986).
Hirschman, et al., "Inhibition of human immunodeficiency virus type 1 replication by nonionic block polymer surfactants", J. Med. Virol. 42(3):249-54 (1994).
Iwasaki, et al., "Exacerbation of influenzavirus pneumonia by intranasal administration of surfactant in a mouse model", Arch. Virol., 144: 675-685 (1999).
King, "Rheology of cystic fibrosis sputum after in vitro treatment with hypertonic saline alone and in combination with recombinant human deoxyribonuclease l", Am. J. Respir. Crit. Care Med., 156(1):173-7 (1997).
King, et al., "The effect of structured and unstructured pre-operative teaching: a replication", Nurs. Res., 31(6):324-9 (1982).
King, et al., "The role of mucus gel viscosity, spin ability, and adhesive properties in clearance by simulated cough", Biorheology, 26:737-745 (1989).
Kurashima, et al, "A pilot study of surfactant inhalation for the treatment of asthmatic attack", Arerugi, 40(2):160-3 (1991).
Lipp, et al, "Solving medical problems with chemical engineering", Chemtech, 42-57 (Mar. 1997).
Nanaumi, et al., "Properties of mixed monolayers of DPPC and viscoelasticity-giving substances", Colloids & Surfaces B: Bioinformatics, 17:167-174 (2000).
Otrisal® Dosierspray Losung in Novaris Consumer Health, Germany.
Papineni and Rosenthal, "The size distribution of droplets in the exhaled breath of healthy human subjects", J. Aerosol Med., 10(2): 105-116 (1997).
Patton and Platz, "Pulmonary delivery of peptides and proteins for systemic action", Adv. Drug Del. Rev., 8:179-196 (1992).
Piret, et al., "Sodium lauryl sulfate, a microbicide effective against enveloped and nonenveloped viruses", Curr. Drug Targets, 3(1)17-30 (2002).
Rosenblum, "fish", Grolier Multimedia Encyclopedia, 2006, Grolier Online, accessed Nov. 21, 2006 (gme.grolier.com/cgi-bin/article?assetid=0106750-0).
Rote Liste Service: "Rote Liste 2002", Editio Cantor Verlag, Aulendorf (2002).
Rudt and Muller, "In vitro phagocytosis assay of nano- and microparticles by chemiluminescence. I. Effect of analytical parameters, particle size and particle concentration", J. Controlled Release, 22: 263-272 (1992).
Tabata and Ikada, Macrophage phagocytosis of biodegradable microspheres composed of L-lactic acid/glycolic acid homo- and copolymers, J. Biomed. Mater. Res., 22: 837-858 (1988).
Takebayashi, et al., "Role of tachykinins in airway responses to ozone in rats", J. Appl. Physiol. 85: 442-450 (1998).
Tansey, "The challenges in the development of metered dose inhalation aerosols using ozone-friendly propellants", Spray Technol. Market, 4: 26-29 (1994).
The Merck Index, $12^{th}$ Edition, Merck & Co., Inc., Whitehouse Station, NJ, pp. 1089.
Tibby, et al. "Exogenous surfactant supplementation in infants with respiratory syncytial virus bronchiolitis", Am. J. Respir. Crit. Care Med., 162(4 Pt 1): 1251 (2000).
Timsina, et al, Drug delivery to the respiratory tract using dry powder inhalers, Int. J. Pharm., 101: 1-13 (1995).

(56) References Cited

OTHER PUBLICATIONS

Visser, "An invited review Vander Waals and other cohesive forces affecting powder fluidization", *Powder Technology*, 58: 1-10 (1989).
Vollenbroich, et al., "Mechanism of inactivation of enveloped viruses by the biosurfactant surfactin from *Bacillus subtilis*", *Biologicals*, 25(3):289-97 (1997).
Wanatabe, et al., "Immunogenicity and protective efficacy of replication-incompetent influenza virus-like particles", *Journal of Virology*, 76(2):767-773 (2002).
Wikipedia, "Hypertonic" Wikipedia, 2006, accessed Nov. 21, 2006 (en.wikipedia.org/wiki/Hypertonic).
Zanen and Lamm, The optimal particle size for parasympathicolytic aerosols in mild asthmatics, *J. Int. J. Pharm.*, 114: 111-115 (1995).
Zasadzinski, et al., "The physics and physiology of lung surfactants", *Current Opinion in Colloid & Interface Science*, 6:506-513 (2001).
Im Hof, et al., "In vivo determination of surface tension in the horse trachea and in vitro model studies," *Respiration Physiology*, 109: 81-93 (1997).

\* cited by examiner

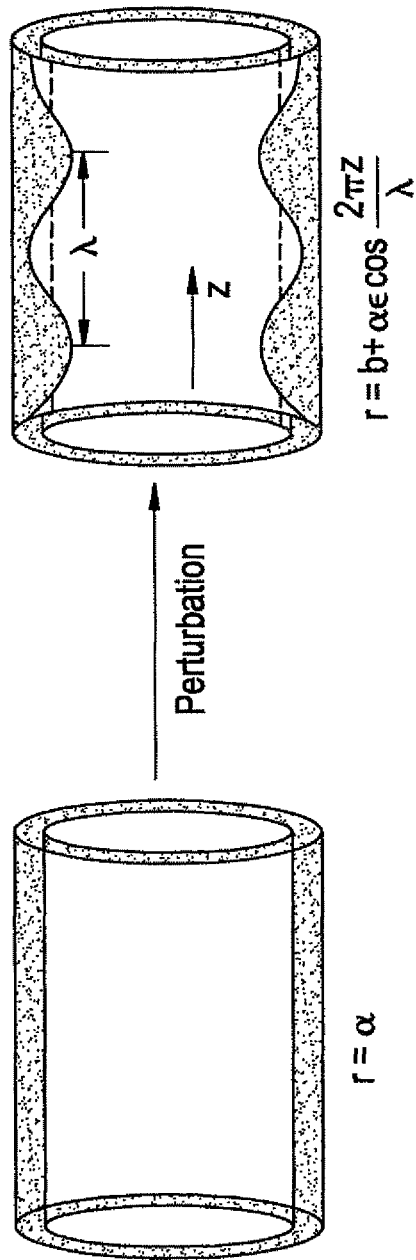

$$r = b + \alpha\epsilon\cos\frac{2\pi z}{\lambda}$$

Assume evolution of perturbation amplitude has the form:

$$\epsilon = \epsilon_0 e^{\alpha}$$ — Growth rate

For an incompressible fluid, the initial growth rate (neglecting inertial effects) has the form:

$$\alpha \propto \frac{\gamma}{\mu}\left(\left(\frac{\lambda}{\lambda_{crit}}\right)^2 - 1\right)$$

surface tension

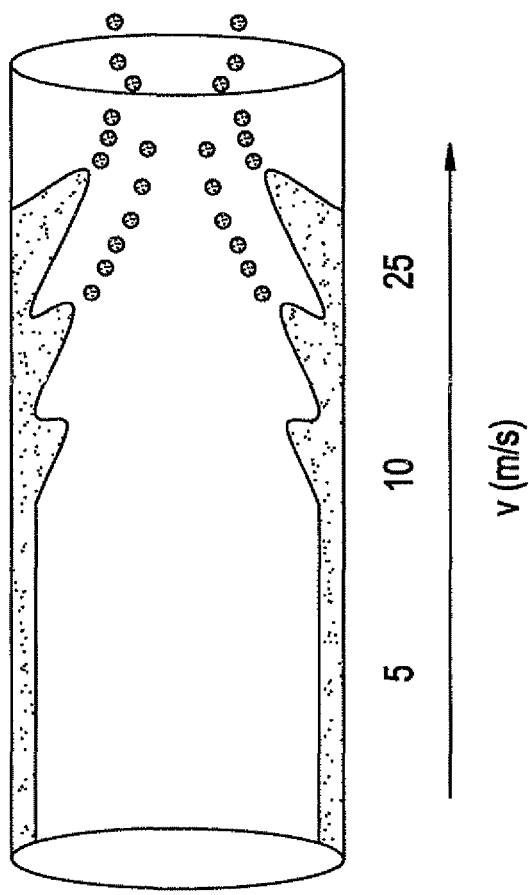

FIG. 5

5μm < d_aero < 10μm → Animal application

1μm < d_aero < 3μm → Human application

Nano - particles < 0.5μm

Valve cap

Air Flow

FIG. 6

METHODS FOR LIMITING SPREAD OF PULMONARY INFECTIONS

FIELD OF THE INVENTION

The present invention is in the field of pulmonary delivery of bioactive molecules to decrease the incidence of viral shedding and other airborne pathogens.

This application is a continuation of U.S. Ser. No. 10/513,165 filed Apr. 28, 2005, now abandoned, entitled "Formulations Limiting Spread of Pulmonary Infections", by David A. Edwards and Howard A. Stone, which is a filing under 35 U.S.C.§371 of PCT/US03/13707 filed with the U.S. Receiving Office of the Patent Cooperation Treaty on May 1, 2003, which claims priority to U.S. Ser. No. 60/377,327, filed May 2, 2002, all of which are herein incorporated in their entirety by reference.

BACKGROUND OF THE INVENTION

Viral and bacterial infections are frequently highly contagious, especially when spread by respiration. The recent reports regarding Sudden Acute Respiratory Syndrome ("SARS"), now known to be caused by a corona virus, are proof of how rapidly an infection can spread when it is transmitted through air contact. Other diseases such as influenza spread by air contact, and rapidly reach epidemic proportions, with high numbers of fatalities in elderly and immunocompromised populations.

SARS is a respiratory illness that has recently been reported in Asia, North America, and Europe. As of Apr. 20, 2003, about 198 suspect cases of SARS and 38 probable cases of SARS had been reported in the United States. In general, SARS begins with a fever greater than 100.4° F. [>38.0° C.]. Other symptoms may include headache, an overall feeling of discomfort, and body aches. Some people also experience mild respiratory symptoms. After 2 to 7 days, SARS patients may develop a dry cough and have trouble breathing.

The primary way that SARS appears to spread is by close person-to-person contact. Most cases of SARS have involved people who cared for or lived with someone with SARS, or had direct contact with infectious material (for example, respiratory secretions) from a person who has SARS. Potential ways in which SARS can be spread include touching the skin of other people or objects that are contaminated with infectious droplets and then touching your eye(s), nose, or mouth. This can happen when someone who is sick with SARS coughs or sneezes droplets onto themselves, other people, or nearby surfaces. It also is possible that SARS can be spread more broadly through the air or by other ways that are currently not known. At present there is no treatment or means of prevention for SARS, other than supportive care.

TB, or tuberculosis, is a disease caused by bacteria called *Mycobacterium tuberculosis*. The bacteria can attack any part of your body, but they usually attack the lungs. TB disease was once the leading cause of death in the United States. In the 1940s, scientists discovered the first of several drugs now used to treat TB. As a result, TB slowly began to disappear in the United States. But TB has come back. Between 1985 and 1992, the number of TB cases increased; more than 16,000 cases were reported in 2000 in the United States.

TB is spread through the air from one person to another. The bacteria are put into the air when a person with TB disease of the lungs or throat coughs or sneezes. People nearby may breathe in these bacteria and become infected. When a person breathes in TB bacteria, the bacteria can settle in the lungs and begin to grow. From there, they can move through the blood to other parts of the body, such as the kidney, spine, and brain. TB in the lungs or throat can be infectious. This means that the bacteria can be spread to other people. TB in other parts of the body, such as the kidney or spine, is usually not infectious. People with TB disease are most likely to spread it to people they spend time with every day. This includes family members, friends, and coworkers. People who are infected with latent TB do not feel sick, do not have any symptoms, and cannot spread TB, but they may develop TB disease at some time in the future. People with TB disease can be treated and cured if they seek medical help. Even better, people who have latent TB infection but are not yet sick can take medicine so that they will never develop TB disease.

Other human viruses are also highly contagious and have no effective treatments other than containment. For example, Respiratory syncytial virus (RSV) is a very common virus that causes mild cold-like symptoms in adults and older healthy children. RSV is the most common respiratory pathogen in infants and young children. It has infected nearly all infants by the age of two years. It can cause serious respiratory infections in young babies, especially those born prematurely, who have heart or lung disease, or who are immunocompromised. Seasonal outbreaks of acute respiratory illness occur each year, on a schedule that is somewhat predictable in each region. The season typically begins in the fall and runs into the spring. RSV is spread easily by physical contact. Touching, kissing, and shaking hands with an infected person can spread RSV. Transmission is usually by contact with contaminated secretions, called foamites, which may involve tiny droplets or objects that droplets have touched. RSV can live for half an hour or more on hands. The virus can also live up to five hours on countertops and for several hours on used tissues. RSV often spreads very rapidly in crowded households and day care centers.

In infants and young children, RSV can cause pneumonia, bronchiolitis (inflammation of the small airways of the lungs), and tracheobronchitis (croup). In healthy adults and older children, RSV is usually a mild respiratory illness. Although studies have shown that people produce antibody against the virus, infections continue to occur in people of all ages. Each year up to 125,000 infants are hospitalized due to severe RSV disease; and about 1-2% of these infants die. Infants born prematurely, those with chronic lung disease, those who are immunocompromised, and those with certain forms of heart disease are at increased risk for severe RSV disease. Those who are exposed to tobacco smoke, attend daycare, live in crowded conditions, or have school-age siblings are also at higher risk.

Recently, it has been reported that exogenous surfactant supplementation in infants with respiratory syncytial virus bronchiolitis was beneficial (Tibby, et al. Am J Respir Crit. Care Med 2000 October; 162(4 Pt 1): 1251). Infants with RSV bronchiolitis are deficient in surfactant, both in quantity and ability to reduce surface tension. Evidence suggests surfactant has a role in maintaining the patency of conducting airways. Nineteen ventilated infants (median corrected age 4 wk) received either two doses of surfactant (Survanta, 100 mg/kg) within 24 and 48 h of the beginning of mechanical ventilation, or air placebo. Static lung compliance and resistance measured in infants in the placebo-treated group but not in the surfactant-treated group became progressively worse over the first 30 h following enrollment. The principle means of treatment remains supportive however, and there is no means of limiting spread other than isolation.

Influenza is another common viral infection for which there is no effective treatment, and containment is a major option to limit spread of disease. Influenza is caused by three viruses—Influenza A, B and C. Type A is usually responsible for the large outbreaks and is a constantly changing virus. New strains of Type A virus develop regularly and cause new epidemics every few years. Type B causes smaller outbreaks, and Type C usually causes mild illness. In the United States, infection with influenza A and B leads to 20,000 deaths and over 100,000 hospitalizations each year. Influenza is transmitted person to person via contagious droplets that are formed when someone sneezes or coughs. Certain individuals are at higher risk from complications of influenza and therefore vaccination is recommended for these high risk groups. This includes people aged 50 or older, people with diabetes, or with medical conditions affecting the heart, lungs (i.e. asthma) or kidneys; health care workers and anyone with a weakened immune system (HIV, etc.). Supplies of vaccine are limited each year, but after high-risk people have been vaccinated, anyone desiring protection can request vaccination.

Approximately 8 million children and adolescents between 6 months and 17 years of age have one or more medical conditions that put them at increased risk of influenza-related complications. These children should be given the first vaccine available. Such children include those with chronic disorders of the heart or lungs (such as asthma and cystic fibrosis), children who have required regular medical follow-up or hospitalization during the preceding year because of chronic metabolic diseases (including diabetes mellitus), kidney dysfunction, sickle cell anemia, or immunosuppression. Adolescents who will be in the second or third trimester of pregnancy during the influenza season are another subceptible group that should be vaccinated.

For unvaccinated individuals who have been exposed to people with known influenza, especially if the exposed individual has risk factors, potential use of antiviral medication for more than 2 weeks and vaccination may help prevent illness. For mild illness in people who are not at high-risk, the treatment of influenza is frequently just supportive and includes bed rest, analgesics for muscle aches and pains, and increased intake of fluids. Treatment is usually not necessary for children, but may be prescribed if the illness is diagnosed early and the patient is at risk of progression to more severe disease. Among individuals in high-risk groups (elderly, immunosuppressed, chronic heart, lung or kidney conditions) influenza may be quite severe and can lead to complications.

Epidemics of respiratory infections are not limited to humans. Foot-and-mouth disease virus (FMDV) is the etiologic agent of foot-and-mouth disease (FMD), which is a disease of cattle, swine, and other cloven-footed animals. FMD is characterized by the formation of vesicles on the tongue, nose, muzzle, and coronary bands of infected animals. The virus has several unique characteristics make it one of the most economically devastating diseases in today's world, The ease with which it may be transmitted by contact and aerosol, combined with its enhanced ability to initiate infections, virtually ensures that most, if not all, animals in a herd will contract FMD. The long-term survival of FMDV in infected animals' tissues and organs, especially when refrigerated, offers an opportunity for its national and international transmission through the food chain. Multiple serotypes and numerous subtypes reduce the effectiveness and reliability of vaccines. The possible development of carriers in vaccinated animals and those that have recovered from FMD provides additional potential sources of new outbreaks. These features create a disease that can have a major economic impact on farmers and entire nations. The foot and mouth disease (FMD) epidemic in British livestock remains an ongoing cause for concern, with new cases still arising in previously unaffected areas (Ferguson, et al., *Nature* 2001 414(6861): 329). Epidemiological analyses have been vital in delivering scientific advice to government on effective control measures. Using disease, culling and census data on all livestock farms in Great Britain, the risk factors determining the spatiotemporal evolution of the epidemic and of the impact of control policies on FMD incidence were analyzed. The species mix, animal numbers and the number of distinct land parcels in a farm are central to explaining regional variation in transmission intensity. The parameter estimates obtained in a dynamic model of disease spreading to show that extended culling programs were essential for controlling the epidemic to the extent achieved, but demonstrate that the epidemic could have been substantially reduced in scale had the most efficient methods been used earlier.

Viral shedding is thought to be the mechanism that bioaerosols containing infectious pathogens are generated in one organism and passed to the outside, where they can be inhaled by another animal or human. The devastating consequences that uncontrolled viral shedding can have on livestock were seen in the hoof and mouth disease outbreak in the U.K, where 2030 confirmed cases resulted in the mandatory slaughter of 4 million animals. Recently, more attention is being given to the threat of bioterrorism and the similar risk that a sudden outbreak of disease poses to livestock in the U.S.

Airborne infection is one of the main routes of pathogen transmission in livestock. Aerosols composed of mucus droplet originating in the lungs and nasal cavities are produced when the animal coughs. These bioaerosols can contain pathogens that transmit the disease upon inhalation by exposed animals. Presently, no measures have been taken to redress the potential for the rapid spread of infection by decreasing the rate of bioaerosol production by infected livestock. Such measures would have to carefully consider the physiological mechanism and relevance of bioaerosol production.

It is therefore an object of the present invention to provide a method and formulations for use in decreasing or limiting spread of pulmonary infections, especially viral or bacterial infections.

It is another object of the present invention to provide formulations for treatment of humans or animals to limit infectivity.

SUMMARY OF THE INVENTION

Formulations have been developed for pulmonary delivery to treat or reduce the infectivity of diseases such as viral infections, especially tuberculosis, SARS, influenza, cytomegalovirus and RSV in humans and hoof and mouth disease in animals. Formulations for pulmonary administration include a material that significantly alters physical properties such as surface tension, surface elasticity and bulk elasticity of lung mucus lining fluid, which may be a surfactant and, optionally, a carrier. The formulation may be administered as a powder where the particles consist basically of the material altering surface properties, such as surface tension and/or surface and/or bulk elasticity. The carrier may be a solution, such as an alcohol, although an aqueous solution may be utilized, or a material mixed with the material altering surface properties to form particles. These may include proteins such as albumin or polysaccharides such as dextran, which also has surface active properties, or polymers such as polyethylene oxide (PEO) or biodegradable synthetic polymers which can be used to encapsulate or deliver the materials to be delivered. Drugs, especially antivirals or antibiotics, may optionally be included with the formulation. These may be administered with or incorporated into the formulation.

In a preferred embodiment, the formulations are administered either as a powder or aerosol, preferably prior to or shortly after infection, to decrease or prevent infection and then viral shedding. The formulation is administered in an amount sufficient to decrease surface instabilities in the liquid lining the airways of the lung, i.e., to damp the rate of droplet formation from lung fluid. The material that significantly alters physical properties such as surface tension and surface elasticity preferably will be selected and administered in an amount to increase surface elasticity and alter surface tension within the lung.

One example demonstrates reduced aerosolization using ethanol alone or more significantly, in combination with a surfactant, DPPC. Another example shows using a suitable quantity and size of a macromolecule, such as 50K Da dextran, or PEO, can also significantly reduce aerosolization. Another example shows that using an additive, such as 500K Da dextran, such that bulk fluid Theological properties are substantially altered, can lead to enhanced aerosolization.

BRIEF DESCRIPTION OF THE DRAWINGS

FIG. 1 is a graph showing the average airspeed (m/sec) through each of the Generations 1-15 of Weibel's model for the human airway, from the trachea (Generation 0) to the terminal bronchioles (Generation 15) (E.R. Weibel, *Morphometry of the Human Lung*. Springer, Heidelberg, 1963). Mucus bioaerosol generation is not possible at normal breathing rates (1 L/Sec; ◆), however is possible in the upper airways during a forceful cough (10 L/Sec; ☐).

FIG. 2 is a graph of the viscosity of a solution of PEO is considerable only for large strain rates.

FIGS. 4a, 4b and 4c are schematics of bioaerosol formation.

FIG. 5 is a schematic of a formulation for nebulization, and method of administration.

FIG. 6 is a schematic of an apparatus to measure bioaerosol quantity.

DETAILED DESCRIPTION OF THE INVENTION

Figure 3:
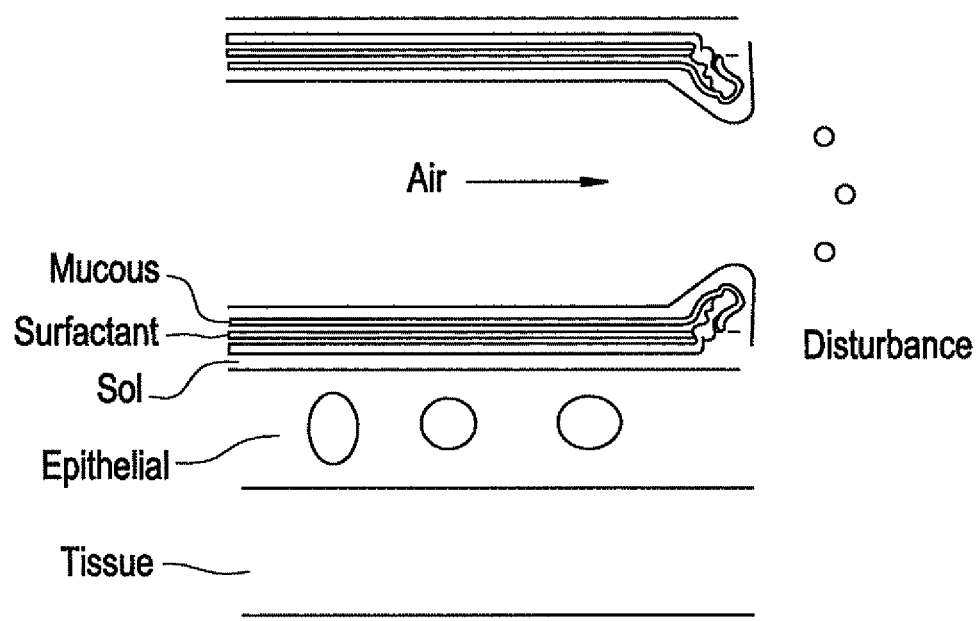
FIG. 3 is a schematic of the approximate scheme of the organization of fluids in the airways.

Prophylactic administration of a formulation containing one or more materials that alter physical properties such as surface tension and surface elasticity of lung mucus lining fluid is used to reduce viral shedding and spread of bacterial infection.

Lung mucociliary clearance is the primary mechanism by which the airways are kept clean from particles present in the liquid film that coats them. The conducting airways are lined with ciliated epithelium that beat to drive a layer of mucus towards the larynx, clearing the airways from the lowest ciliated region in 24 hours. The fluid coating consists of water, sugars, proteins, glycoproteins, and lipids. It is generated in the airway epithelium and the submucosal glands, and the thickness of the layer ranges from several microns in the trachea to approximately 1 micron in the distal airways in humans, rat, and guinea pig.

A second important mechanism for keeping the lungs clean is via momentum transfer from the air flowing through the lungs to the mucus coating. Coughing increases this momentum transfer and is used by the body to aid the removal of excess mucus. It becomes important when mucus cannot be adequately removed by ciliary beating alone, as occurs in mucus hypersecretion associated with many disease states. Air speeds as high as 200 m/s can be generated during a forceful cough. For such high air speeds the onset of unstable sinusoidal disturbances at the mucus layer have been observed. This disturbance results in enhanced momentum transfer from the air to the mucus and consequently accelerates the rate of mucus clearance from the lungs. Experiments have shown that this disturbance is initiated when the air speed exceeds some critical value that is a function of film thickness, surface tension, and viscosity (M. Gad-El-Hak, R. F. Blackwelder, J. J. Riley. *J. Fluid Mech.* (1984) 140:257-280). Theoretical predictions and experiments with mucus-like films suggest that the critical speed to initiate wave disturbances in the lungs is in the range of 5-30 m/s.

I. Formulations

Formulations have been developed to limit infections of the respiratory system, especially viral infections of the lung. The formulations include a material which significantly alters physical properties such as surface tension and surface elasticity of lung mucus lining fluid as the principle active ingredient, carrier materials, and optionally, anti-viral or anti-bacterial drugs. In a preferred embodiment, the formulations are an organic suspension for enhanced delivery to the lung, that forms liquid aerosol particles of 3 to 7 μm diameter loaded with a high concentration of active molecules such as proteins, surfactants, and/or biopolymers, which reduce viral shedding.

Definitions

The term low toxicity as used herein refers to a solvent that does not cause permanent long term damage to body cells or organs.

The term aerosol as used herein refers to any preparation of a fine mist of particles, typically less than 10 microns in diameter, which can be in solution or a suspension, whether or not it is produced using a propellant. Aerosols can be produced using standard techniques, such as ultrasonication or high pressure treatment.

The terms solution or dissolve as used herein refer to compositions in which the bioactive agent is present as a monomolecular dispersion. Concentration ranges are from greater than 0 up to 500 mg/ml. Residual solvents in pharmaceuticals are organic volatile chemicals that are used or produced in the syntheses of drug substances, or excipients, or in the preparation of drug products which are not completely removed by processing.

Biocompatible refers to Class 3 residual solvents that do not cause any long term harmful effects on bodily tissues or cells. This is defined in the U.S. Federal Register vol. 62, number 85, pages 24301-24309 as solvents with low toxic potential to man; no health based exposure limit is needed. Class 3 solvents have PDE's of 50 mg or more per day.

As used herein, the term surfactant refers to any agent which preferentially adsorbs to an interface between two immiscible phases, such as the interface between water and an organic polymer solution, a water/air interface or organic solvent/air interface. As used herein, a surfactant may be any material that significantly alters physical properties such as surface tension and surface elasticity of lung mucus lining fluid, and includes amphiphilic materials, polymers such as polyethylene oxide, and certain polysaccharides and proteins.

A. Surfactants

Surfactants generally possess a hydrophilic moiety and a lipophilic moiety, such that, upon absorbing to microparticles, they present moieties to the external environment that do not attract similarly-coated particles, thus reducing particle agglomeration. Surfactants may also promote absorption of a drug and increase bioavailability of the drug.

As used herein, a particle "incorporating a surfactant" refers to a particle with a surfactant on at least the surface of the particle. The particle may be formed entirely of surfactant or surfactant may be incorporated throughout the particle, on the particle surface during synthesis, or coated on the particle after synthesis. The surfactant can be coated on the particle surface by adsorption, ionic or covalent attachment, or physically "encapsulated" by the surrounding matrix. The surfactant can be, for example, incorporated into controlled release particles, such as polymeric microspheres.

Surfactants which can be used include phosphoglycerides. Exemplary phosphoglycerides include phosphatidylcholines, such as the naturally occurring lung surfactant, L-alpha.-phosphatidylcholine dipalmitoyl (DPPC]). The use of surfactants endogenous to the lung may avoid the need for the use of non-physiologic surfactants. Other exemplary surfactants include diphosphatidyl glycerol (DPPG); 1,2-Dipalmitoyl-sn-glycero-3-phospho-L-serine (DPPS); 1,2-Distearoyl-sn-glycero-3-phosphatidylcholine (DSPC); 1,2-Distearoyl-sn-glycero-3-phosphoethanolamine (DSPE); fatty alcohols such as polyethylene glycol (PEG); polyoxyethylene-9-lauryl ether; a surface active fatty acid, such as palmitic acid or oleic acid; sorbitan trioleate (Span 85); glycocholate; surfactin; a poloxomer; a sorbitan fatty acid ester such as sorbitan trioleate; tyloxapol and a phospholipid. Surfactants which can be included in the formulation to improve their aerosolization properties include phosphoglycerides.

The surfactant is preferably specifically targeted to mucus droplet formation. Some flexible polymers, such as polyethylene oxide (PEO), dramatically increase viscosity at high strain rates. Three strategies to decrease the emission of airborne particles will be investigated. The approach, motivation, and variables to be tested in these systems are as follows: High tension preparation (DPPC based formulation); Low tension preparation (DPPC with DSPC); and High tension/high elasticity preparation (DPPC with dextran or PEO).

The surfactant can also be used as a particle stabilizer for suspensions. Other additives, such as some inorganic salts (10 mM to 5 M), and viscosity modifying agents such as the water soluble polymers poly(ethylene glycol) and carboxymethylcellulose (0.1% to 10% (w/v)), may also be used to enhance solubility, stability or absorption.

Other surfactants which have been reported to have antiviral properties may also be used. For example, the efficacy of sodium lauryl sulfate (SLS), a sulfated anionic chaotropic surfactant, and dextran sulfate (DS), a polysulfated carbohydrate, against herpes simplex virus (HSV) and human immunodeficiency virus (HIV) infections evaluated in cultured cells and in different murine models of HSV infection have been reported. Results showed that both SLS and DS were potent inhibitors of the infectivities of various HSV-1 and HSV-2 strains. Pretreatment of HIV-1 (strain NL4-3) with SLS also reduced its infectivity to 1G5 cells. DS prevented the binding of HSV to cell surface receptors and therefore its entry into cells. Piret, et al., *Curr Drug Targets.* 2002 February; 3(1):17-30. Surfactin is a cyclic lipopeptide antibiotic and biosurfactant from *Bacillus subtilis*, and reported to be active against a broad spectrum of different viruses. These viruses include Semliki Forest virus (SFV), herpes simplex virus (HSV-1, HSV-2), suid herpes virus (SHV-1), vesicular stomatitis virus (VSV), simian immunodeficiency virus (SIV), feline calicivirus (FCV), and murine encephalomyocarditis virus (EMCV), as reported by Vollenbroich, et al., *Biologicals,* 1997 September; 25(3):289-97. In vitro experiments showed biphasic virus inactivation kinetics for enveloped viruses during treatment. Inactivation of enveloped viruses, especially herpes- and retroviruses, was much more efficient than that of non-enveloped viruses. For those viruses susceptible to its action, surfactin was active at 25 microM in medium containing 5% fetal calf serum (FCS). Concentrations up to 80 microM of surfactin led to a titre reduction of >$4.4^{10}$ CCID50/ml for HSV-1 in 15 min and for SIV and VSV in 60 min.

Nonionic block polymer surfactants such as polyethylene oxide have been reported to inhibit human immunodeficiency virus type 1 replication by nonionic block polymer surfactants, Hirschman, et al., *J Med. Virol.* 1994 March; 42(3):249-54. Eight block copolymers of hydrophilic polyoxyethylene and hydrophobic polyoxypropylene were examined for their effects on the replication of human immunodeficiency virus type 1 (HIV-1) in H9 cells. Although the polymers decreased cellular replication, they did not appear to be toxic to the cells; rather, they seemed to arrest cellular growth. Three triblock copolymers were found to inhibit HIV replication at low concentrations. Maximum inhibition was achieved at concentrations of 50 micrograms/ml by day 5 following infection. The combination of azidothymidine with both HIV-1-inhibitory and noninhibitory copolymers resulted in antagonistic effects. An increase in viral replication was observed compared to treatment with copolymers or azidothymidine alone. These copolymers should be useful in the study of the mechanism of HIV replication in cell cultures and may yield clinically useful compounds in combination therapies for HIV infection.

Kurashima, et al, *Arerugi* 1991 February; 40(2):160-3, reported on a study to determine whether surfactant inhalation has a therapeutic effect in asthmatic attack. Eleven patients with asthmatic attack whose conditions were stable for at least six hours before the study were randomly assigned to placebo or surfactant inhalation. Respiratory function tests and blood gas analysis were performed before and 20 minutes after the treatment. After placebo administration, no significant change was observed from baseline in pulmonary functions. After surfactant administration (1 ml; 10 mg per milliliter), respiratory functions were markedly improved in all patients. The mean (+/−SE) change in the FVC, FEV1.0, MMF, delta N2 and PaO2 was, respectively, an increase of 11.7+/−1.3% (p less than 0.001), an increase of 27.3+/−4.4% (p less than 0.05), an increase of 33.3+/−4.7% (p less than 0.05), a decrease of 31+/−8.4% p less than 0.05) and an increase of 13.4+/−0.8% (p less than 0.05). No difference was detected in PaCO2 after surfactant inhalation. This study indicates that airway surfactant is involved in the pathogenesis of bronchoobstruction of the patients with asthma.

In addition, many biopolymers and some large proteins are surface active in the sense of increasing the surface elasticity or, by virtue of their presence in the bulk solution, increasing the bulk elasticity.

B. Carriers and Aerosols for Administration

Carriers can be divided into those for dry powder formulations and for administration as solutions.

1. Liquid Formulations

Aerosols for the delivery of therapeutic agents to the respiratory tract have been developed. See, for example, Adjei, A. and Garren, *J. Pharm. Res.*, 7: 565-569 (1990); and Zanen, P. and Lamm, J.-W. *J. Int. J. Pharm.*, 114: 111-115 (1995).

Choi, et al. 2001. *Proc. Natl. Acad. Sci.* 98. 11103-11107, describes nebulization of proteins in ethanol as a means of delivering proteins to the lungs. The ethanol system has many potential benefits: the organic nature of the ethanol can stabilize the tertiary and quaternary structure of the proteins; the ethanol can act as a biocide and limit microbial contamination of the suspension; higher dosing can be achieved because the amount of drug in suspension is not limited by solubility; the non-polar nature of the ethanol can allow inclusion of lipophilic drugs; and the ethanol in solution can act as a enhancer to drug penetration, similar to transdermal systems.

The solvents useful in the compositions are low toxicity organic (i.e. nonaqueous) class 3 residual solvents, such as ethanol, acetone, ethyl acetate, tetrahydrofuran, ethyl ether, and propanol. The solvent is selected based on its ability to readily aerosolize the composition. The solvent should not detrimentally react with the active ingredient. An appropriate solvent should be used that dissolves the active ingredient or forms a suspension of the active ingredient. A suspension is also referred to as a dispersion herein.

The solvent moreover should be sufficiently volatile to enable formation of an aerosol of the solution or suspension. Additional solvents or aerosolizing agents, such as freons, can be added as desired to increase the volatility of the solution or suspension.

Ethanol, isopropanol, and other alcohols are the preferred solvents. Up to 100 mg DPPC can be suspended in one milliliter of ethanol. The effects of ethanol are well characterized, and its systemic and local toxicities are understood. Permeability appears to increase with the chain length of the alcohol. Also, the concentration of the aqueous alcohol appears to an important factor when considering these systems. Generally, drug transport increased with ethanol concentration. However, there is a limit to the enhancement effect of alcohols in relation to its concentration.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated.

The solubility of proteins in ethanol, as in nearly all other organic solvents is very low and even under optimal conditions is usually far below 1 mg/ml. A protein solution can be treated in such way to form nano-particles once added to ethanol. Experiments have confirmed that lipids are very soluble in ethanol. For example, up to 100 mg/mL of DPPC was successfully dispersed in ethanol at room temperature before causing sedimentation of aggregates. Polysaccharides such as dextran and carageenan precipitate in ethanol at concentrations higher than 0.5 mg/mL. Microscopy shows that the polymer formed micron size polymer sphere. Addition of surfactant to the suspension to try to disperse the polymer leads to the formation of surfactant emulsion drop but did not have a significant effect on the polymer dispersion. DLS can be used to measure the size and size distribution of the ethanol solutions. A suitable apparatus is an ALV DLS/SLS-5000 spectrometer/goniometer (ALV-Laser GmbH, Langen, Germany). The light source for the experiments is an Argon Ion laser of wavelength 514.5 nm (Coherent, Calif.). Light scattered by the sample is detected at an angle of 90° from the transmitted beam, where the effects of reflection are minimized. The sample cell is placed in a toluene bath maintained at a temperature of 25° C.

Nonaqueous suspensions of lipids (6 to 100 mg/mL) can be prepared in absolute ethanol using a reusable PARI LC Jet+ nebulizer (PARI Respiratory Equipment, Monterey, Calif.), A starting volume of 9 ml was charged in the reservoir, and aerosol particles were produced. This can be analysed in an Aerosizer APS 3321 particle size analysis system (TSI, St. Paul, Minn.). Once formed the aerosol is injected at a constant flow rate in a chamber. The particles are confined to the centerline of an accelerating flow by sheath air and then pass through two broadly focused laser beams. Light is scattered by the particles and is collected by an ellipitical mirror whose role is to focus the collected light onto a solid-state photodetector. The light pulses are detected and converted in electrical pulses. It is known that the separation between the two beam is of the order of 90-100 μm, and the total flow in the detection chamber is 5 L/min, so the aerodynamic radius of the particles can be determined from the time between the peaks of the two pulses the velocity for each individual particle. This instrument is designed for particles with time of flight (TOF) ranging from about 800 ns to 4.1 μs (size of the particles from 0.3 to 20 μm).

2. Dry Powder Formulations

The geometry of the airways is a major barrier for drug dispersal within the lungs. The lungs are designed to entrap particles of foreign matter that are breathed in, such as dust. There are three basic mechanisms of deposition: impaction, sedimentation, and Brownian motion (J. M. Padfield. 1987. In: D. Ganderton & T. Jones eds. Drug Delivery to the Respiratory Tract, Ellis Harwood, Chicherster, U.K.) Impaction occurs when particles are unable to stay within the air stream, particularly at airway branches. They are adsorbed onto the mucus layer covering bronchial walls and cleaned out by mucocilliary action. Impaction mostly occurs with particles over 5 μm in diameter. Smaller particles (<5 μm) can stay within the airstream and be transported deep into the lungs. Sedimentation often occurs in the lower respiratory system where airflow is slower. Very small particles (<0.6 μm) can deposit by Brownian motion. This regime is undesirable because deposition cannot be targeted to the alveoli See N. Worakul & J. R. Robinson. 2002. In: Polymeric Biomaterials, $2^{nd}$ ed. S. Dumitriu ed. Marcel Dekker. New York Another consideration when designing particles for aerosol delivery is the surface to volume ratio, which contributes to the high efficiency deposition. Particles with a large size and a low mass have proven most effective at deep lung deposition. This quality can be characterized by the aerodynamic diameter $d_{aer}$, as defined: $d_{aer}=d\sqrt{\rho}$, where d is the diameter of the particle and ρ its density (see Gonda, I. In Topics in Pharmaceutical Sciences. 1991, D. J. A. Crommelin and K. K. Midha, Eds. (Medpharm Scientific, Stuttgart, 1992) pp 95-115). Previous calculations by Heyder J. et al. ibid. 17, 811 (1986); Edwards, D. A., ibid, 26, 293 (1995) have shown that the optimum aerodynamic diameter for the particles to achieve 60% deposition of particle inhaled has to be around approximately 3 μm. The preferred size range as used herein is between approximately 3 and 7 microns in diameter, although particles up to 15 microns can be utilized.

Drug delivery by inhalation represents a well established mode of administration of low molecular weight pharmaceuticals for various lung disorders, with a promise for general noninvasive systemic delivery of drugs. Several biopharmaceutical companies are developing methods for pulmonary delivery of peptides and proteins, with one such product already in clinical use (the enzyme DNAse produced by Genentech for the treatment of symptoms of cystic fibrosis in children). Furthermore, there is no evidence that inhaling autologous proteins presents significant immune issues.

A number of pharmaceutical preparations for pulmonary delivery of drugs has been developed. For example, U.S. Pat. No. 5,230,884 to Evans et al., discloses the use of reverse micelles for pulmonary delivery of proteins and peptides. Reverse micelles are formed by adding a little water to a nonpolar solvent (e.g. hexane) to form microdroplets. In this medium, a surfactant (detergent) will orient itself with its polar heads inward, so that they are in contact with the water and the hydrophobic tails outward. The tiny droplets of water are surrounded by surfactant, and the protein to be delivered is dissolved in the aqueous phase.

U.S. Pat. No. 5,654,007 to Johnson et al., discloses methods for making an agglomerate composition containing a medicament powder (e.g. proteins, nucleic acids, peptides, etc.) wherein a nonaqueous solvent binding liquid (a fluorocarbon) is used to bind the fine particles into aggregated units. The agglomerate composition has a mean size ranging from 50 to 600 microns and is allegedly useful in pulmonary drug delivery by inhalation.

PCT/US97/08895 by Massachusetts Institute of Technology discloses particles made of a biodegradable material or drug, which have a tap density less than 0.4 g/cm$^3$ and a mean diameter between 5 μm and 30 μm.

PCT/EP97/01560 by Glaxo Group Limited discloses spherical hollow drug particulates for use in pulmonary delivery.

These materials can be used for delivery of formulation to the lungs, modified as necessary to deliver the correct dosage of surface modifying agent at a desired rate and to a preferred location within the lung.

Dry powder formulations ("DPFs") with large particle size have improved flowability characteristics, such as less aggregation (Visser, J., *Powder Technology* 58; 1-10 (1989)), easier aerosolization, and potentially less phagocytosis. Rudt, S, and R. H. Muller, *J. Controlled Release,* 22: 263-272 (1992); Tabata, Y., and Y. Ikada, *J. Biomed. Mater. Res.,* 22: 837-858 (1988). Dry powder aerosols for inhalation therapy are generally produced with mean diameters primarily in the range of less than 5 microns. Ganderton, D., J. *Biopharmaceutical Sciences,* 3:101-105 (1992); and Gonda, I. "Physico-Chemical Principles in Aerosol Delivery," in Topics in Pharmaceutical Sciences 1991, Crommelin, D. J. and K. K. Midha, Eds., Medpharm Scientific Publishers, Stuttgart, pp. 95-115, 1992, although a preferred range is between one and ten microns in aerodynamic diameter. Large "carrier" particles (containing no drug) have been co-delivered with therapeutic aerosols to aid in achieving efficient aerosolization among other possible benefits. French, D. L., Edwards, D. A. and Niven, R. W., *J. Aerosol Sci.,* 27: 769-783 (1996).

As noted above, particles can be formed solely of surface modifying agent, or combined with a drug or excipient. Suitable materials include proteins such as albumin, polysaccharides such as dextran, sugars such as lactose, and synthetic polymers. Preferred polymers are biodegradable. Most preferred are those such as polyethyleneoxide copolymers, which have surfactant properities. Materials other than biodegradable polymers may be used to form the particles including other polymers and various excipients. Other materials include, but are not limited to, gelatin, polyethylene glycol, polyethylene oxide, trehalose, and dextran, Particles with degradation and release times ranging from seconds to months can be designed and fabricated, by established methods in the art.

The synthetic polymers may be tailored to optimize particle characteristics including: i) interactions between the agent to be delivered and the polymer to provide stabilization of the agent and retention of activity upon delivery; ii) rate of polymer degradation and thus drug release profile; iii) surface characteristics and targeting capabilities via chemical modification; and iv) particle porosity.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The preferred mean diameter for aerodynamically light particles for inhalation is at least about 5 microns, for example between about 5 and 30 microns, most preferably between 3 and 7 microns in diameter. The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different therapeutic agent may be administered to target different regions of the lung in one administration.

As used herein, the phrase "aerodynamically light particles" refers to particles having a tap density less than about 0.4 g/cm.sup.3. The tap density of particles of a dry powder may be obtained using a GeoPyc™ (Micrometrics Instrument Corp., Norcross, Ga. 30093). Tap density is a standard measure of the envelope mass density. The envelope mass density of an isotropic particle is defined as the mass of the particle divided by the minimum sphere envelope volume in which it can be enclosed. Features contributing to low tap density include irregular surface texture and porous structure.

Inertial impaction and gravitational settling of aerosols are predominant deposition mechanisms in the airways and acini of the lungs during normal breathing conditions. Edwards, D. A., *J. Aerosol Sci.,* 26: 293-317 (1995). The importance of both deposition mechanisms increases in proportion to the mass of aerosols and not to particle (or envelope) volume. Since the site of aerosol deposition in the lungs is determined by the mass of the aerosol (at least for particles of mean aerodynamic diameter greater than approximately 1 microns), diminishing the tap density by increasing particle surface irregularities and particle porosity permits the delivery of larger particle envelope volumes into the lungs, all other physical parameters being equal. The low tap density particles have a small aerodynamic diameter in comparison to the actual envelope sphere diameter. See, for example, U.S. Reexamination Patent No. 37,053 to Edwards, et al.

3. Active Ingredients

The formulations disclosed herein can be used for the delivery of a variety of molecules, especially antivirals and antiinfective molecules including antibiotics. Examples of macromolecules include proteins and large peptides, polysaccharides and oligosaccharides, and DNA and RNA nucleic acid molecules and their analogs having therapeutic, prophylactic or diagnostic activities. Nucleic acid molecules include genes, antisense molecules that bind to complementary DNA to inhibit transcription, and ribozymes. The agents to be incorporated can have any of a variety of biological activities, being, for example vasoactive agents, neuroactive agents, hormones, anticoagulants, immunomodulating agents, cytotoxic agents, prophylactic agents, antibiotics, antivirals, antisense, antigens, or antibodies. Preferred agents are antiviral, steroid, bronchodilators, and antibiotics. The formulations may include an active ingredient for local delivery within the lung, or for systemic treatment.

Macromolecules, such as proteins and nucleic acids can be dissolved in some organic solvents, e.g. in ethanol, at relatively high concentrations provided that certain critical guidelines are followed. For example, the protein is preferably lyophilized from an aqueous solution having a pH different, preferably remote, from the isoelectric point of the protein. See Bromberg & Klibanov, *Proc. Natl. Acad. Sci. USA*, 92, 1262-1266 (1995), the disclosure of which is incorporated herein by reference. The solubility of macromolecules in organic solvents can be enhanced by certain additives, such as some inorganic salts, detergents, and water soluble polymers such as poly(ethylene glycol) and carboxymethylcellulose. Alternatively, biomacromolecular dispersions or suspensions in the form of microcrystals or lyophilized powders suspended in organic solvents can be used to make aerosols for pulmonary delivery. Proteins are usually not irreversibly damaged in such systems. The advantages of nonaqueous formulations for pulmonary delivery include stability against microbial contamination and a greater (compared to water) ease of the aerosol formation due to their volatility.

II. Administration of Surfactant Formulations to the Respiratory Tract

A. Methods of Administration

The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorbtion occurs. The alveoli are covered by a thin epithelium without cilia or a mucus blanket and secrete surfactant phospholipids. J. S. Patton & R. M. Platz. 1992. *Adv. Drug Del Rev.* 8: 179-196

The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung (Gonda, I. "Aerosols for delivery of therapeutic an diagnostic agents to the respiratory tract," in Critical Reviews in Therapeutic Drug Carrier Systems, 6:273-313 (1990). The deep lung, or alveoli, are the primary target of inhaled therapeutic aerosols for systemic drug delivery.

Inhaled aerosols have been used for the treatment of local lung disorders including asthma and cystic fibrosis (Anderson et al., *Am. Rev. Respir. Pls.*, 140: 1317-1324 (1989)) and have potential for the systemic delivery of peptides and proteins as well (Patton and Platz, *Advanced Drug Delivery Reviews*, 8:179-196 (1992)). Considerable attention has been devoted to the design of therapeutic aerosol inhalers to improve the efficiency of inhalation therapies. Timsina et. al., *Int. J. Pharm.*, 101: 13 (1995); and Tansey, I. P., *Spray Technol. Market*, 4: 26-29 (1994).

Aerosol dosage, formulations and delivery systems may be selected for a particular therapeutic application, as described, for example in Gonda, I. "Aerosols for delivery of therapeutic and diagnostic agents to the respiratory tract," in Critical Reviews in Therapeutic Drug Carrier Systems, 6:273-313, 1990; and in Moren, "Aerosol dosage forms and formulations," in: Aerosols in Medicine, Principles, Diagnosis and Therapy, Moren, et al., Eds. Esevier, Amsterdam, 1985.

The formulation may be administered alone or in any appropriate pharmaceutical carrier for administration to the respiratory system. Typical apparatus which may be used for administration to humans include metered dose inhalers (MDI), dry powder inhalers (DPI), and nebulizers. The formulation is administered in an amount effective to decrease infectivity and/or symptoms of the infection.

The particles can be in a liquid such as saline or a powder and can be co-delivered with larger carrier particles 50-100 µm in diameter not including a therapeutic agent.

Delivery is achieved by one of several methods. For example, the patient can mix a dried powder of pre-suspended protein with ethanol and then nebulize it. It may be more appropriate to use a pre-nebulized solution, regulating the dosage administered and avoiding possible loss of suspension. After nebulization, it may be possible to pressurize the aerosol and have it administered through a metered dose inhaler (MDI). Nebulizers create a fine mist from a solution or suspension, which is inhaled by the patient. The devices described in U.S. Pat. No. 5,709,202 to Lloyd, et al, can be used. An MDI typically includes a pressurized canister having a meter valve, wherein the canister is filled with the solution or suspension and a propellant. The solvent itself may function as the propellant, or the composition may be combined with a propellant, such as freon. The composition is a fine mist when released from the canister due to the release in pressure. The propellant and solvent may wholly or partially evaporate due to the decrease in pressure. FIG. 5 is a schematic of a formulation for nebulization, and method of administration.

Formulation may be administered to animals such as racehorses, breeding livestock, or endangered captive animals to protect these animals from infection by viral shedding. This may be accomplished by placing a nebulizer system near watering stations and triggering production of the aerosol as animals either approach or leave the station. Formulation may be sprayed over the animals as they walk through chutes or pens, or sprayed from spray trucks or even crop dusting type airplanes.

Surfactant may be administered at the onset of viral outbreak to prevent spread of the disease to epidemic levels. Animals within a 10-kilometer radius of a FMD outbreak are currently deemed infected. These animals are subsequently slaughtered and disinfected. This aerosol system may be administered immediately to animals within this 10-kilometer radius zone and a further prescribed buffer zone outside this area to assure containment of the outbreak. The aerosol can then be administered for as long as is necessary to ensure success, i.e. beyond the normal period between first infection and symptom expression.

Figures 1, 2:
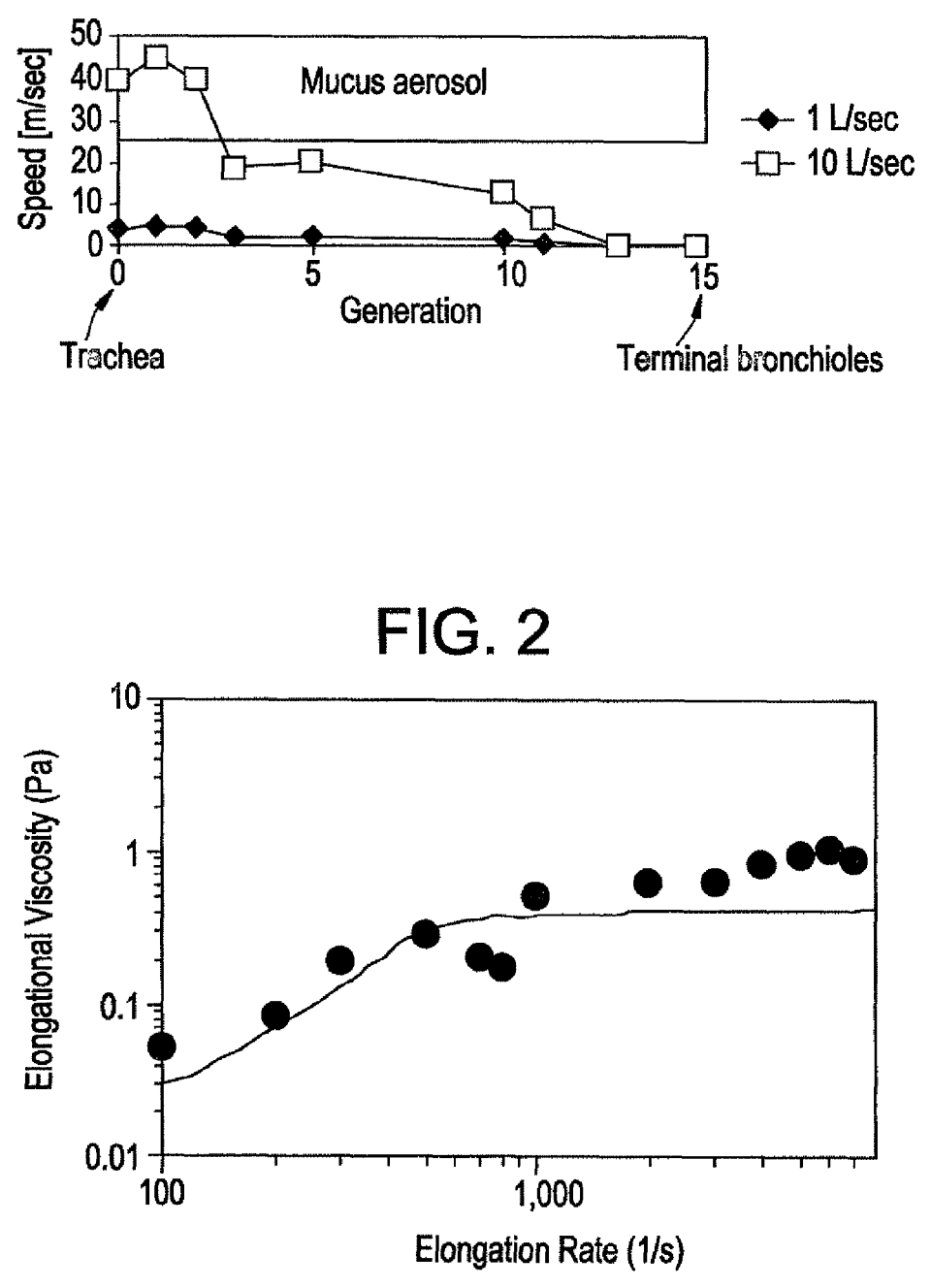

An effective amount of formulation to be delivered can be determined as follows, referring to FIGS. 1-3. This is based in part upon the following observations:

A first-order analysis of the stability of a uniform thin film of liquid coating the inside of a cylindrical tube was performed. An infinitesimal axisymmetric sinusoidal perturbation is imposed on the initially uniform film to query whether surface area minimization will cause the disturbance to grow or decay. Taking the surface integral and keeping the volume constant, it was found that the perturbation increases surface area for wavelengths less than the cylinder circumference while the surface area is decreased for wavelengths greater than the cylinder circumference. Thus for a given tube diameter a disturbance wavelength greater than the critical wavelength must be excited to initiate the sinusoidal disturbance. It is believed that when such a sinusoidal disturbance is excited by high speed airflow within the lung minute droplets can shear off, generating a mucus bioaerosol. The correlation between the reported airspeed required for bioaerosol generation (25 m/s) and the airspeed required for exciting sinusoidal wave disturbances (5-30 m/s) supports bioaerosol formation conditions. In an infected organism, the mucus often contains a high concentration of the pathogen and the bioaerosol can thus function as an efficient transmission vehicle for the pathogen.

Weibel's model (E. R. Weibel. *Morphometry of the Human Lung*. Springer, Heidelberg, 1963) describes the human lungs as comprising 24 airway generations, starting with the trachea as generation 0, the main bronchi 1, the lobar bronchi 2 and so on with the alveolar sacs being represented as airway generation 23. Given the characteristic diameter and number of tubes of each generation and the normal rate of breathing taken as 1 L/s, the average airspeed through each generation was calculated and compared to the average airspeed through each generation that would arise with a cough expelling air from the airways at 10 L/s (airspeed=[volume flow rate]/[total x-sectional area per generation]).

FIG. 1 demonstrates the effect of air speed on airway generation calculated from characteristic healthy human lung data. For expiratory flow rates of 1 L/s, the normal breathing flow rate, the air speed is well below 25 m/s for all generations. For flow rates of 10 L/s, a flow rate characteristic of a forceful cough, the air speed is greater than 25 m/s in generations 0-2. This shows that coughing can produce air speeds capable of creating mucus aerosols in the upper airways from the trachea down to the lobar bronchi. This is consistent with literature reports that only the upper airways are involved in mucus aerosol generation.

This data suggests that one can reduce the amount of expelled bioaerosol and thus the pathogen transmission rate by increasing the air speed required to shear off mucus droplets. For example, if bioaerosol formation is taken to be proportional to the total surface area of the lung being exposed to air speeds greater than the critical value, then altering the properties of the mucus coating such that the critical air speed increases from 25 to 40 m/s would decrease the amount of bioaerosol generated by 75% (only generation 1 would have supercritical air speeds during a cough, as can be seen from the plot).

Decreasing bioaerosol production is thus seen to be a matter of modifying the properties of the mucus such that the critical air speed required to shear off mucus droplets is increased. While it is known that the critical air speed depends on the mucus viscosity, thickness, and surface tension, the precise nature of the relationships is a matter of debate. The critical air speed for wave formation in vitro increases with decreasing film thickness and increasing viscosity (C. A. Evrensel, R. U. Khan, S. Elli, P. E. Krumpe. *J. Biomech. Eng.* (1993) 115:262-27) yet other researchers argue that the critical air speed increases with increasing film thickness for some surface tension values while it increases with decreasing film thickness for other surface tension values.

While some modification of the properties of mucus in the upper airways may be possible with only limited side effects, the surface wave disturbance associated with mucus aerosol generation enhances momentum transfer and thus aids in the removal of excess mucus. Furthermore, the efficacy of mucociliary clearance is sensitive to changes in mucus viscosity as evidenced by patients with chronic bronchitis and cystic fibrosis. Modification of the mucus properties in the upper airways may yield undesirable side-effects associated with diminished mucus clearance. However, such an intervention should only be necessary in the upper airways since toxicity associated with decreased oxygen transport or alveolar collapse would be entirely avoided. It is therefore preferable to use a treatment that specifically targets mucus droplet formation while leaving other mucus characteristics unchanged.

In the preferred embodiment, this treatment involves the deposition of small amounts of a long chain polymer with a desirable elongational viscosity. Elongational viscosity is the tendency of a solution to resist flow at high strain rates (V. Bergeron, D. Bonn, J. Y. Martin, L. Vovelle. *Nature*. (2000) 405:772-775). FIG. 2 shows an example of the elongational viscosity of 0.25 g/L polyethyleneoxide (PEO) as a function of strain rate (S. W. Clarke, J. G. Jones, D. R. Oliver. *J. Appl Physiol*. (1970)). This rheological property is exploited in firefighting by the addition of small quantities of polymer to the water that dramatically increases the range of the water jet emerging from the hose. The polymer achieves this feat in part by suppressing the jet break-up as it leaves the nozzle. As with the jet break-up, airflow shearing of the mucus lining that generates mucus droplets is a process characterized by very high strain rates. Accordingly, the addition of small amounts of polymer, such as PEO, may contribute to a significantly higher critical air speed required to generate bioaerosols. The primary advantage of such an approach is that it would leave the Theological properties of the mucus unchanged at the low strain rates associated with mucociliary clearance and wave formation.

Figure 4B:
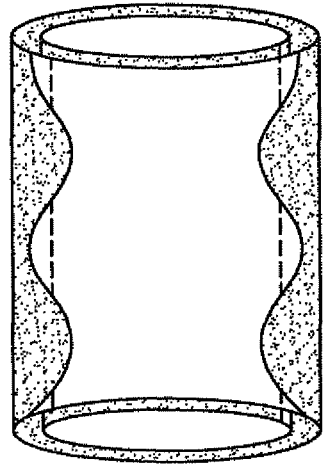

FIG. 3 is a schematic of the approximate scheme of the organization of fluids in the airways. FIGS. 4a and 4b are schematics showing how the fluid layer is disturbed and forms waves. The amplitude of these waves increases in infection or inflammation, leading to formation of droplets, as shown in FIG. 4c. Introduction of surfactant dampens the growth of this instability by allowing for surface tension gradients. The variables leading to the onset and dynamics of instability in the mucous layer are surface tension, elasticity, viscosity and film thickness. One can decrease bioaerosolization by modifying one or more of these variables without affecting mucociliary clearance.

In Vitro Testing of Bioaerosol Transmission

The following in vitro method can be used to test the effect of exogenous surfactants, including flexible polymers, on bioaerosol generation in the airways. A "cough machine" (M. King, J. M. Zahm, D. Pierrot, S. Vaquez-Girod, E. Puchelle. *Biorheology*. (1989) 26:737-745) will be used to control air speed experienced by simulated mucus lining of the airway. Radiolabeled nanoparticles simulating viral particles will be incorporated in the fluid, and a filter will be placed at the exit of the cough machine to collect the aerosol droplets generated. A variety of compounds will be added to alter shear viscosity, elongational viscosity, and surface tension, and the test will be repeated at varying air velocities, below, including, and above 25 m/s.

The formulation will simultaneously lower mucus droplet production and minimally change variables such as mucus clearance to assure safety. First, three systems are used (A-C) according to three physical hypotheses. The first system (A), comprised solely of a synthetic dipalmitoyl phosphatidyl choline (DPPC), the primary lung surfactant constituent, will test the effect of increasing mucus surface tension. The second system (B), comprised of a mixture of DPPC and synthetic DSPC (a second constituent of natural lung surfactant), will test the effect of lowering mucus surface tension. The third system (C), comprised of DPPC and a polysaccharide (dextran), will test the effect of increasing surface elasticity. Each of these systems will be tested in a simple in vitro apparatus designed to create surface instabilities, thus measuring the ability of the surfactant systems to reduce the instabilities. The in vitro system will be created of a mixing cup from which a cylindrical tube extends vertically downward. The cup and tube will be rotated at a fixed rate. Water will be poured into the cup at a given flow rate, and will create a film of liquid of some defined thickness within the annulus of the tube. This film will fall by gravity from the bottom of the tube. An airstream will be blown through the tube at a rate to break the falling annulus of water into droplets soon after departing from the tube. The distance the water film falls from the tube prior to breakup will be measured. Each of the surfactant systems (A-C) will be added to the water in the mixing cup in ratios similar to those expected on delivery of the systems to lung fluid (typically, large mammal lung fluid volumes are in the 20-40 mL range). The precise compositions of systems A-C will be changed such that the instability is most significantly dampened, i.e. such that the distance of film fall from the tube prior to breakup is maximized. The two best surfactant systems in the in vitro model will be carried into live animal model systems, and simultaneously toxicity will be tested.

Toxicity Studies

Compounds to be administered can be tested for non-toxicity. For example, preliminary in vitro studies were conducted to test the toxicity of ethanol solutions upon addition to monolayers of fibroblast cells. NIH 3T3 fibroblasts were plated onto glass Lab-Tek™ coverslip chambers (NUNC, Rochester, N.Y.) and grown to confluence. The cells were then exposed to a solution of 30% ethanol in 10% FBIS DMEM for 10 seconds and returned to the incubator after several washes with 10% FBS in DMEM. After 15 minutes the cells were exposed to 10 µM Cell-Tracker™ Green CMFDA (Molecular Probes, Eugene, Oreg.) for 30 min. The cells were then washed several times with 10% FBS DMEM and placed in a 37° C., 5% $CO_2$ microscope chamber. The CMFDA stain readily enters the cell and if the cell is alive it becomes enzymatically modified and cannot leave. Thus viable cells will fluoresce brightly while dead cells will not. The cells were imaged with an inverted fluorescence microscope. An image of the monolayer shows brightly stained cells indicating that exposure of cells to as much as 30% ethanol for 10 seconds is insufficient to cause cell death.

In vivo toxicity studies determine which of the most effective formulations of the in vitro studies are the least toxic. Animals will be administered the prepared surfactant formulations in ethanol and intravenous blood samples will be collected. The blood samples will be analyzed for blood alcohol content. Also, tracheal lavage will provide information about damage to lung tissue resulting from administration of the preparations.

In Vivo Experimentation

In vitro effects of various surfactant formulations on surface tension, elasticity, and viscosity can be measured. Ideally, the surfactant would spread evenly over the surface of the mucosal layer to prevent the necking and budding of mucus droplets, which are believed to be created primarily by high air speeds such as those resulting from coughing (King, M., et. al *Biorheology*, 26; 737-745, 1989). Since the mucus layer contains the particulate matter of the lung, including infectious microbes and virus particles, the addition of the mucus droplets to an individual's bioaerosol may be responsible for more rapid transmission of airborne diseases. By preventing the formation of mucosal aerosol droplets, administered pulmonary surfactant would reduce the airborne transmission of disease. The test subjects will be hamsters and pigs. The pulmonary systems and breathing patterns of these paradigms are most well known and are most conducive to studying bioaerosols (Boren, H G. *Arch Intern Med* 1970 September; 126(3):491-495).

Ideally, an attenuated influenza virus will be used to test the efficacy of surfactant. By dissolving the exhalent filter and running an assay to test for the presence of influenza particles, one can see if the surfactants lower the number of particles emanating from the subject. Other models may be used. The first is fluorochrome-tagged bacteriophage, which is simple and inexpensive to perform in the laboratory. The benefit of using fluorochrome tagged bactriophage is that the results of the study are easily quantifiable. The exhalent of the subject will be collected on a filter; by simply measuring the level of fluorescence on the filter paper, the relative amount of bacteriophage can be determined. A limitation is that a bacteriophage may not behave the same way that a true virus particle would. A genetically modified, replication-incompetent influenza, missing the NS2 gene (Wanatabe, et al. 2002) can also be used. As a non-infectious strain, these virus-like-particles (VLP's) would be ideal to model influenza in the lungs of a test subject.

The following technique will be used to administer the surfactant. Hamsters will be placed in a Plexiglas restraining tube that will serve as a head-only exposure flow plethysmograph (Takebayashi, et al. *J Apps Physiol* 85: 442-450, 1998). Different tube sizes will used to accommodate the animals. The tube will be fitted with a silicone rubber gasket designed to fit snugly around the animal's neck and seal the head from the rest of the body. Once the animal is in the tube, a large piston will be moved into place behind the animal. The piston will serve to prevent the animal from moving and to seal the body chamber from the outside air. Air displaced at the body surface as the animal breathed, passed across a pneumotachograph (8-mm diameter fitted with a screen filter) attached to a differential pressure transducer (model 163PC01D75, Omega Engineering, CT). The resulting flow signal will be analyzed by a computer program (BUXCO, Troy, N.Y.) that will compute minute ventilation, tidal volume, breathing frequency, inspiratory (TI), and expiratory time (TE) on a breath-by-breath basis and report the average of each of these values every minute. The cranial end of the tube will be inserted through a port in the Plexiglas door of a stainless steel chamber (approximately 145 liters in volume). The animals will first exposed to filtered air for 25 min to adapt the animals to the plethysmographs. Subsequently, the viral marker will be administered with the filtered air to deposit in the lungs for 30 min. Based on the minute volumes, the concentration of viral marker in the chamber, the exposure time, and an estimate of 10% deposition rate in the lungs, the amount of viral marker can be normalized according to the breathing patterns of the subject. Filtered air will then follow for another 60 min to ensure deposition in the mucosal layer. For each subject, one of our surfactant formulations will be administered for 30 min. Control groups will receive nebulized ethanol.

The administration device will then be modified to add a filter over the cranial end of the tube, and changed at 15 minute time intervals. All air exiting the tube will exit through this filter. As a result, all virus particles emanating from the subject will appear on this filter. Filters will be assayed for the presence of the viral marker. For each subject, the tube will be of one of the following lengths: 10 cm, 25 cm, 50 cm, 75 cm, 1 m. Filters will continue to be changed until the appearance of new viral marker becomes negligible. Throughout this portion of the experiment, the pneumotachograph will continue to be in operation to monitor changes in breathing patterns of the subject.

This can be used to show that the surfactant formulations result in a statistically significant difference in the number of exhaled marker particles from the control, as well as to compare formulations. Using different tubing lengths will indicate whether the surfactant only reduces some subset of exhaled particles, providing new directions for the mechanism of viral shedding. In addition, the use of a pneumotachograph throughout the experiment will provide a preliminary indication of whether or not breathing and coughing rates are affected by the administration of surfactants.

Rats exposed to the above aerosols will be divided into groups according to dosing, time period, and control. Broncheoalveolar lavage will be performed after euthanizing the rats. The fluid will be analyzed for cell type and macrophage activation. Other relevant histopatbology tests will be performed as necessary, and bronchioconstriction will be examined.

B. Patients to be Treated

The formulations can be administered to animals or humans in need thereof. The animals or humans may be infected with, or exposed to, a viral disease. Exemplary viral diseases are foot and mouth disease in animals, and SARS, RSV, cytomegalovirus (CMV) and influenza in humans. The humans may by infected with tuberculosis, or be exposed to allergens or have asthma.

In general, the formulations will be administered by treatment with aerosols or nebulized surfactant. Humans are treated as described above, using a DPI, MDI, or nebulizer. Animals can be walked through enclosed areas where they must breathe the formulation. This will decrease potential infectivity, and lead to decreased spread of the viral particles. Tents for administration of formulation can be made using equipment available currently for use in quarantining equines at sporting events.

Treatment is continued for as long as there is risk of infection or spread of disease, with treatment repeated as necessary to prevent or limit viral shedding. In the case of asthma, allergy and other pulmonary disorders, treatment will be continued to maintain the desired pulmonary parameters.

The present invention will be further understood by reference to the following non-limiting example.

EXAMPLE 1

Reduction in Bioaerosol Exhaled from Lungs

Materials and Methods

An apparatus was constructed to illustrate the ability of a surface-tension and surface-elasticity altering agent to lower the amount of bioaerosol exhaled from the lungs.

Figure 6:
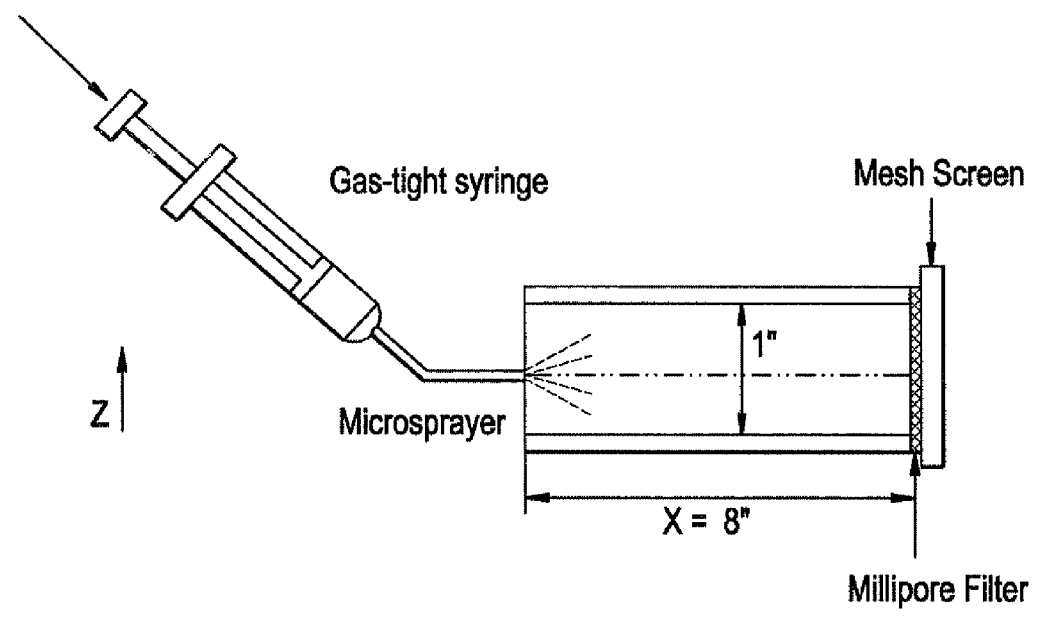

As shown in FIG. 6, a Hamilton Gas-Tight 500 uL syringe was attached to a Penn-Century Microsprayer, 2 inch Rodent Model 1A-1B, and the end of the syringe was placed within a 1 inch ID PVC tube with lengths of 4, 8, and 12 inches. A Millipore Durapore HVPP filter, pore size 0.45 microns, backed by a stainless steel mesh screen, was abutted at the exit of the PVC tube. The syringe plays the role of the exhaled breath, providing a pressure drop that blows air and liquid through the microsprayer and the PVC tube. The breakup of the liquid in the syringe models the breakup of surfactant liquid in the upper airways during an exhaled breath, and the PVC tube mimics the air path from the site of surfactant liquid breakup in the upper airways to the mouth.

100 uL of three kinds of solutions, each containing 1.25 g/L rodamine B (Aldrich) as a florescent marker, i.e., to mimic a pathogen contained within airway fluid, were tested in the syringe. The first solution was distilled water (Millipore Milli-Q Distilled Water), the second was a 80/20 (v/v) ethanol/water solution, and the third was a 80/20 (v/v) ethanol/water solution containing 3.75 g/L of dipalmitoyl phosphatidyl choline (DPPC) (Genzyme). The first solution represents the undisturbed lung lining fluid, the second a lining fluid altered by the presence of ethanol, the third a lining fluid altered by the presence of the surfactant DPPC.

The amount of rodamine that reached the filter following injection of the 100 uL from the syringe through the three different PVC tube types (i.e. 4, 8 and 12 inch tubes) was measured. The goal was to determine whether ethanol, or an ethanol/DPPC mixture, led to less aerosolized rodamine reaching the filter, as a surrogate for the effect of such surface-tension and elasticity alterning materials on the amount of exhaled pathogen following delivery of such materials into the lungs and lung fluid.

Results

Following injection of the solutions and deposition on the filters, the filters were removed and washed with 25 mL methanol (PharmaCo) into 25 mL flasks and then the florescence in the solutions examined with a fluorimeter.

The optimal tube length, where sufficient aerosol exited the tube for measurement, yet not too much aerosol so that the effect of the added ethanol and DPPC on the emitted aerosol particle size could not be measured, was 8 inches.

Figure 7:
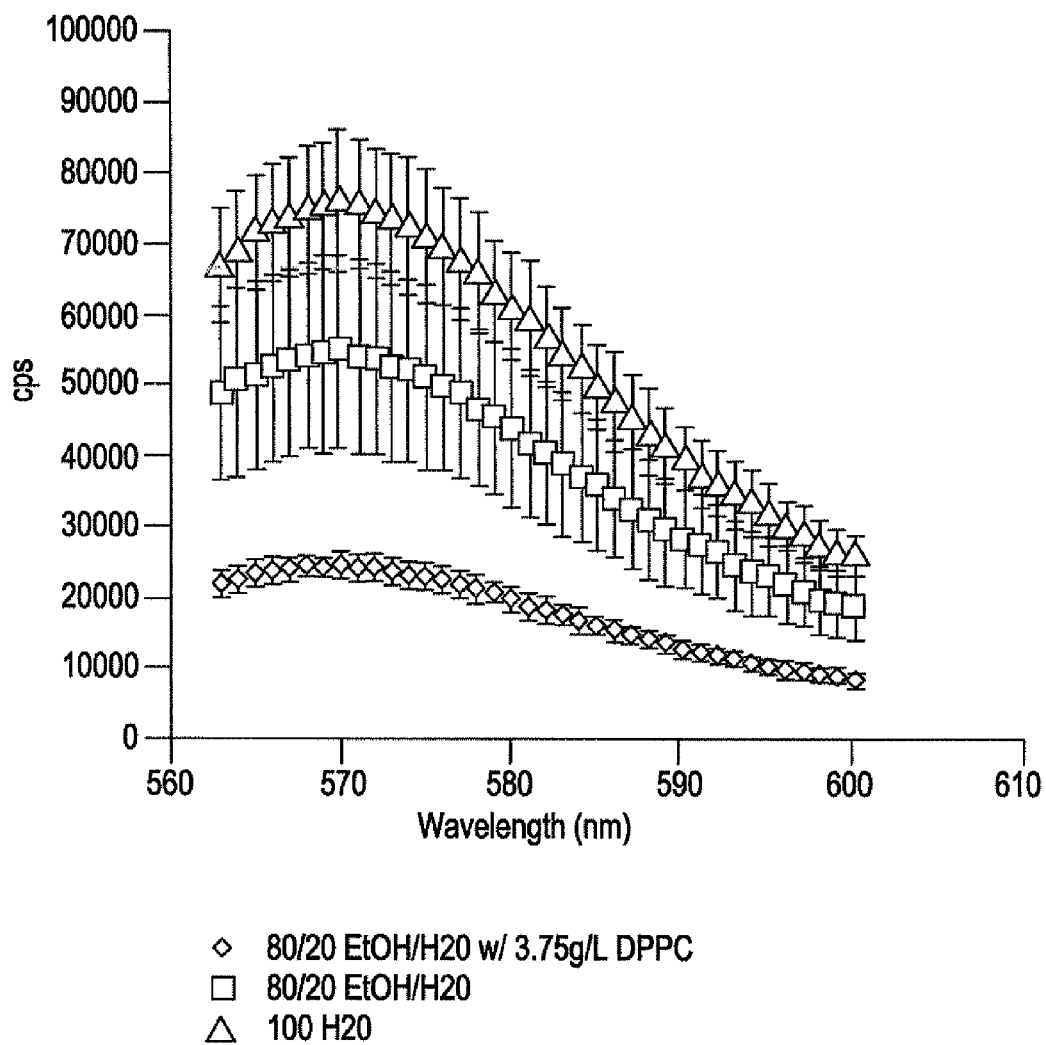
FIG. 7 is a graph of the amount of fluorescence deposited through an apparatus having an 8 inch tube, for water, ethanol, and ethanol containing a surfactant, DPPC.

FIG. 7 shows the florescence spectra (counts per second, obtained from the fluorimeter, versus the wavelenth of the emitted light) for the 8 inch tube experiment. The most fluorescence reaching the filter was observed for the pure water solution. By contrast, the solution with ethanol yielded less aerosol deposited on the filter, and the solution with DPPC/ethanol, had significantly less deposition.

This example shows how materials such as DPPC and ethanol can lead to less aerosol emitting from lung fluids if administered in appropriate amounts and appropriate frequencies.

EXAMPLE 2

Reduction in Bioaerosol using Natural and Synthetic Polymers

Materials and Methods

The same apparatus was used for testing as in Example 1. The first solutions to be aerosolized were 80/20 (v/v) ethanol/water solutions containing 3.75 g/L of POPC and PEO (Genzyme), and the other solutions were 20/80 ethanol/water solutions containing 3.75 g/L of 50K and 500K Da dextrans. The first solutions represent lung lining fluid altered by the presence of two other surfactants, 1-palmitoyl-2-oleoylphosphatidylcholine (POPC) and PEO. The second solutions represent lung lining fluid altered by the presence of a very large macrmolecule (which renders the fluid substantially more viscous) and a smaller macromolecule.

Results

The amount of rodamine that reached the filter following injection of the 100 uL from the syringe through the 8 inch PVC tube was measured as in Example 1. Following injection of the solutions and deposition on the filters, the filters were removed and washed with 25 mL methanol (PharmaCo) into 25 mL flasks and then the florescence in the solutions examined with a fluorimeter.

Figure 8:
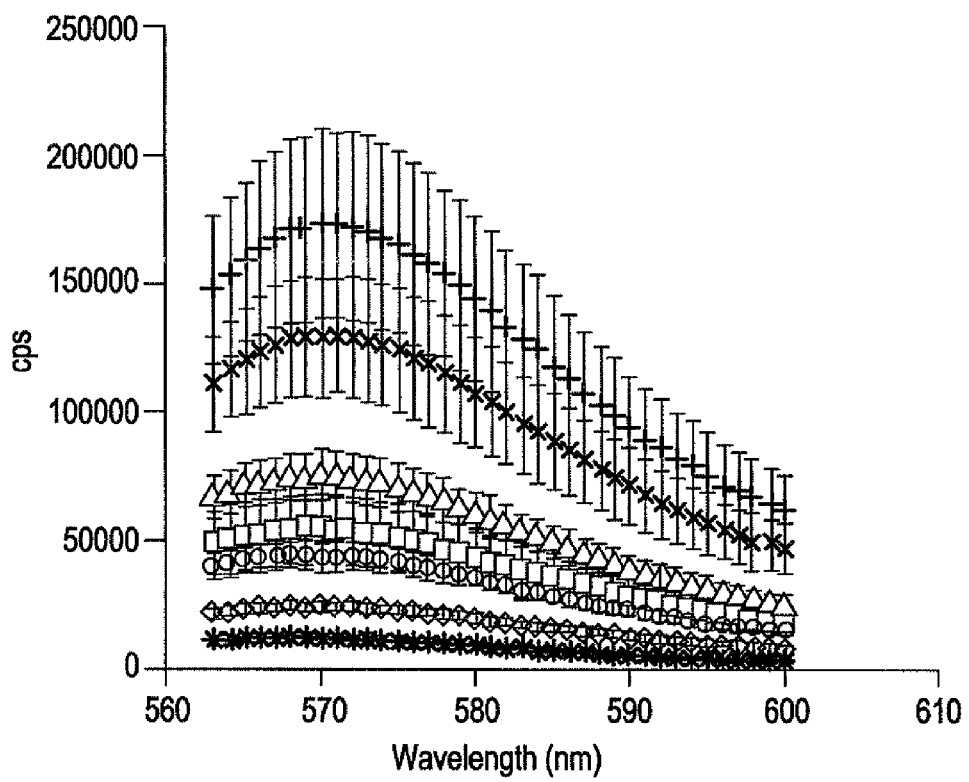
FIG. 8 is a graph of the amount of fluorescence deposited through an apparatus having an 8 inch tube, for water containing surfactant, PEO, a large molecular weight dextran, and a relatively small molecular weight dextran.

FIG. 8 shows the florescence spectra (counts per second, obtained from the fluorimeter, versus the wavelength of the emitted light) for the 8 inch tube experiment. The results are also compared with the results of FIG. 7. The most fluorescence reaching the filter was observed for the large (500K Da)

dextran solution, the next most by the pure water solution. By contrast, the solutions with POPC, PEO, and the 50 KDa dextran, had significantly less deposition.

This example shows how other surfactant materials, such as PEO and POPC, or suitable macromolecules, such as 50K dextran, can lead to less aerosol emitting from lung fluids if administered in appropriate amounts and appropriate frequencies. On the other hand, adding materials such as the 500K Da dextran that change too dramatically bulk fluid properties can lead to greater aerosol emission.

We claim:

1. A method for decreasing aerosolization of droplets of lung fluid from an upper airway comprising administering a dry powder formulation for reducing aerosolization of droplets of lung fluid from the upper airway by increasing the critical air speed required for aerosolization, wherein an active agent to decrease aerosolization consists of microparticles less than 10 microns in diameter in an effective amount for pulmonary administration by a dry powder inhaler or metered dose inhaler, the microparticles comprising a polymeric surface modifying agent delivered to the fluid lining of the lung in an effective amount and molecular weight to increase surface tension, surface elasticity and viscosity of normal lung mucous lining fluid, thereby decreasing droplet formation by the fluid lining of the lung by up to 50% as compared to the droplet formation by the microparticles not including the surface modifying agent, wherein the surface modifying agent is selected from the group consisting of proteins, polysaccharides and synthetic polymers.

2. The method of claim 1, wherein the surface modifying agent is albumin or gelatin.

3. The method of claim 1, wherein the surface modifying agent is trehalose.

4. The method of claim 1, wherein the surface modifying agent is polyethylene glycol.

5. The method of claim 1, wherein the surface modifying agent is dextran.

6. The method of claim 1, wherein the surface modifying agent is polyethylene oxide.

7. The method of claim 1, wherein the particles have a diameter of between approximately 3 and 7 microns.

8. The method of claim 1, wherein the formulation further comprises a compound selected from the group consisting of an antiviral, an antibiotic, a bronchodilator, and a steroid.

9. The method of claim 1, wherein the formulation is administered from a dry powder inhaler or metered dose inhaler.

10. The method of claim 1, wherein the decreased aerosolization reduces the production of bioaerosols containing infectious pathogens.

* * * * *